United States Patent [19]

McKeighen et al.

[11] Patent Number: 5,226,422
[45] Date of Patent: Jul. 13, 1993

[54] TRANSESOPHAGEAL ECHOCARDIOGRAPHY SCANNER WITH ROTATING IMAGE PLANE

[75] Inventors: Ronald E. McKeighen, Woodinville; Frank B. Oaks, Kent; Donald S. Lyle, Mukilteo, all of Wash.

[73] Assignee: Advanced Technology Laboratories, Inc., Bothell, Wash.

[21] Appl. No.: 880,631

[22] Filed: May 8, 1992

[30] Foreign Application Priority Data

May 8, 1991 [GB] United Kingdom ............... 9109881

[51] Int. Cl.⁵ .................................................. A61B 8/12
[52] U.S. Cl. ......................... 128/662.06; 128/662.03; 128/660.08
[58] Field of Search ............... 128/662.06, 662.03, 128/661.01, 660.08; 310/334, 369

[56] References Cited

U.S. PATENT DOCUMENTS

| | | | |
|---|---|---|---|
| 3,779,234 | 12/1973 | Eggleton et al. | 128/662.06 |
| 4,156,158 | 5/1979 | Wilson et al. | 310/369 |
| 4,305,014 | 12/1981 | Borburgh et al. | 310/334 |
| 4,310,957 | 1/1982 | Sachs | 310/334 |
| 4,460,841 | 7/1984 | Smith et al. | 310/334 |
| 4,474,184 | 10/1984 | Harui | 128/662.03 |
| 4,640,291 | 2/1987 | t'Hoen | 310/334 |
| 4,762,002 | 8/1988 | Adams | 128/660.08 |
| 5,085,221 | 2/1992 | Ingebrigtsen et al. | 128/662.06 |
| 5,117,832 | 6/1992 | Sanghvi et al. | 128/662.03 |

*Primary Examiner*—William E. Kamm
*Assistant Examiner*—George Manuel
*Attorney, Agent, or Firm*—W. Brinton Yorks, Jr.

[57] ABSTRACT

A transesophageal echocardiographic scanner includes a rotatable transducer for rotating the image plane of the scanner. The transducer is a circular shaped array of parallel oriented elements which may be operated as a phased or linear array. The transducer is mounted on a bell-shaped backing box with a conical interior surface that directs reverberations from the back of the transducer into damping material which fills the box. The transducer is located in a fluid compartment which is divided by a cover member into an ultrasonic transmission region between the emitting surface of the transducer and the cover, and an adjacent bubble trap region into which bubbles may pass and preferentially remain.

12 Claims, 8 Drawing Sheets

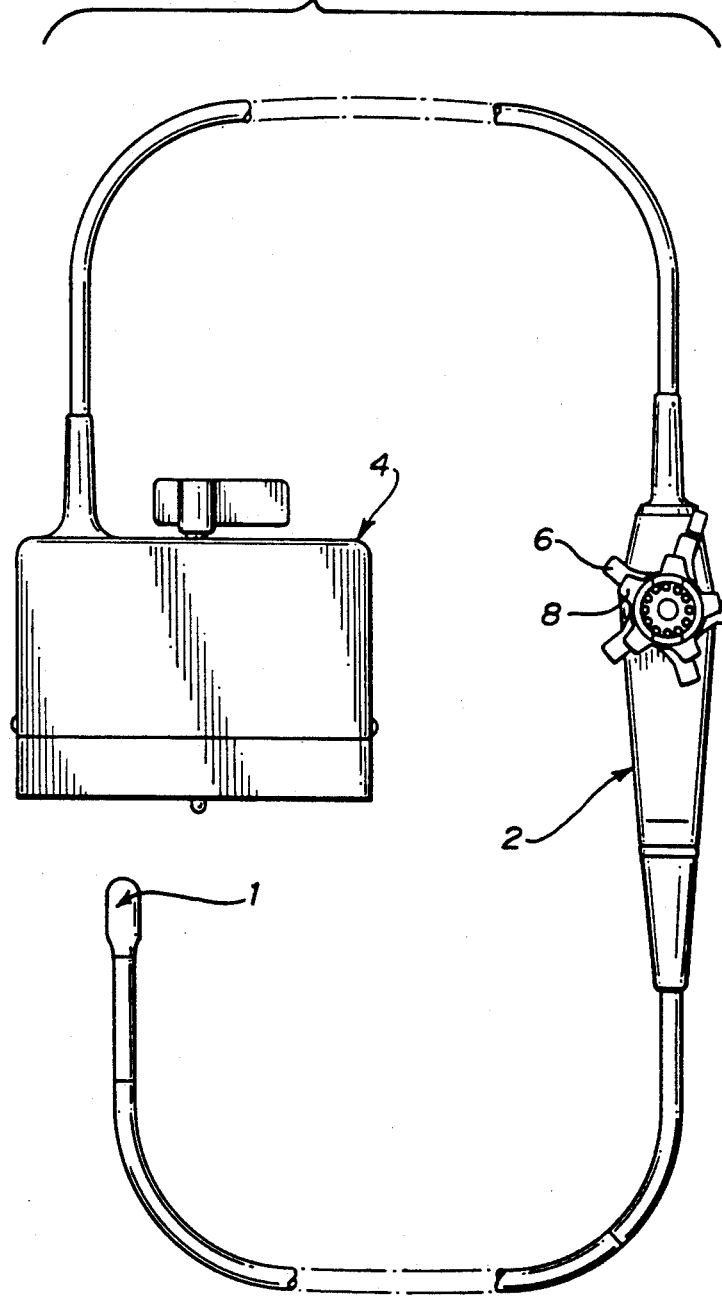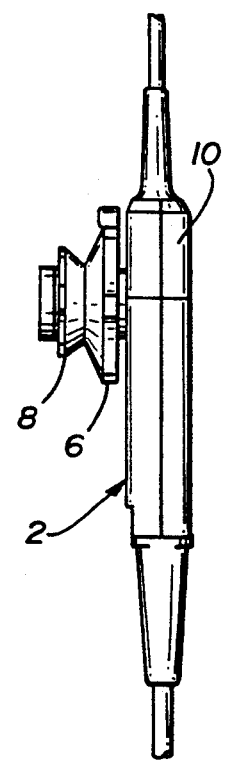

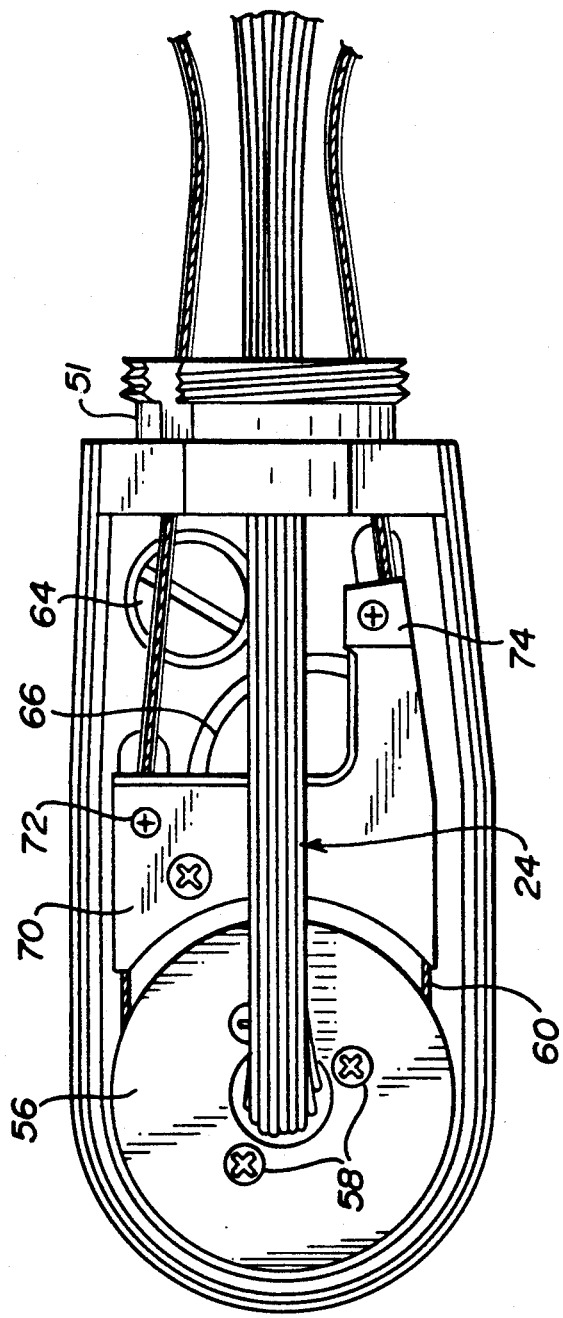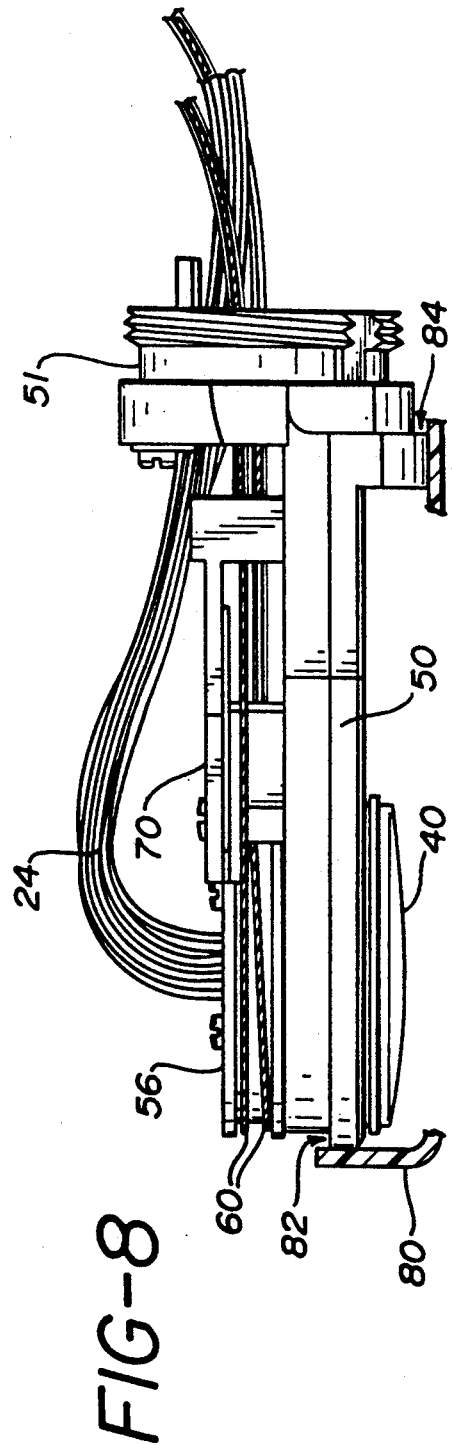

TRANSESOPHAGEAL ECHOCARDIOGRAPHY SCANNER WITH ROTATING IMAGE PLANE

This invention relates to transesophageal echocardiographic scanners for performing ultrasonic examinations of the interior of the body and, in particular, to such scanners in which the ultrasonic transducer is rotated to rotate the scan plane during the examination.

U.S. Pat. No. 4,543,960 (Harui et al.), the contents of which are incorporated herein by reference, describes a transesophageal echocardiographic (TEE) scanhead in which a phased array or linear array transducer is mounted on a rotating base inside the scanhead. As the drawings of that patent shows, the array transducer is a square or rectangular shaped array of piezoelectric elements which is mounted on a cylindrical rotatable base. A pulley is mounted on a shaft extending from the rotatable base, whereby the base and transducer array may be rotated inside the scanhead. A control cable from the control unit of the scanhead passes around the pulley. As the control cable moves by control of the control unit the pulley and rotatable base are turned, thereby rotating the transducer array and hence the image plane.

In accordance with the principles of the present invention a number of improvements are described which improve the manufacture and performance of a TEE scanhead such as that of U.S. Pat. No. 4,543,960. In place of the square or rectangular transducer array a round transducer array is provided, which comprises an array of parallel, linear elements with a round outer periphery. The round transducer array enables the construction of a smaller distal end of the scanhead which is a desirable feature for a transesophageal probe. The sides of the transducer elements which are at reference potential are effectively grounded leaving an exposed periphery of the elements outward from the transducer matching layer. A loop of wire is affixed to this exposed periphery around the perimeter of the array.

The round transducer array is mounted in the larger open end of a conical or bell-shaped housing. Wires attached to the transducer array pass through the end of the housing to which the pulley is attached and through the acoustic damping material inside the housing. The angular interior walls of the housing reflect reverberations from the rear of the transducer array along damping paths of substantial length through the damping material.

An acoustically transmissive cover defines a fluid chamber in front of the transmitting surface of the transducer array. The cover also defines an acoustic window in front of the transducer array and a separate volume comprising a bubble trap into which bubbles pass from the fluid chamber in front of the transducer.

The housing and cover are assembled with a frame which completes the definition of the fluid chamber and also provides a fluid expansion chamber and a fill port.

In the drawings:

FIG. 1 is a top plan view of a TEE scanhead constructed in accordance with the principles of the present invention;

FIG. 1a is a side view of the control unit of the TEE scanhead of FIG. 1;

Figure 3A:
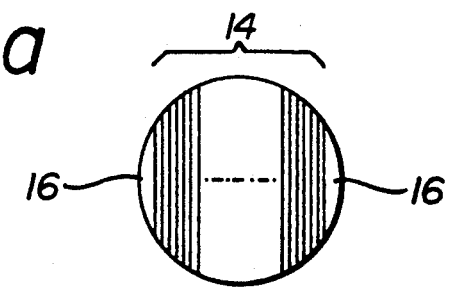
Figure 3B:
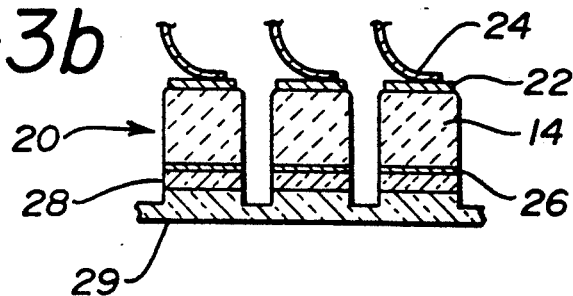
Figure 3C:
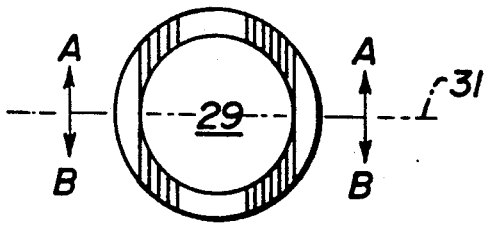
Figure 9:
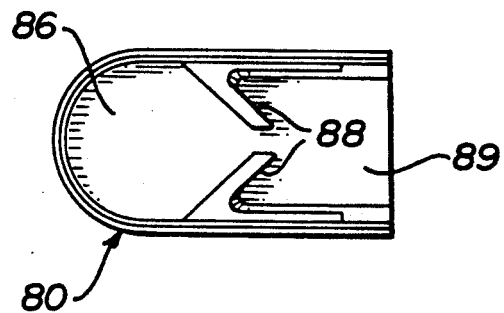
Figure 4:
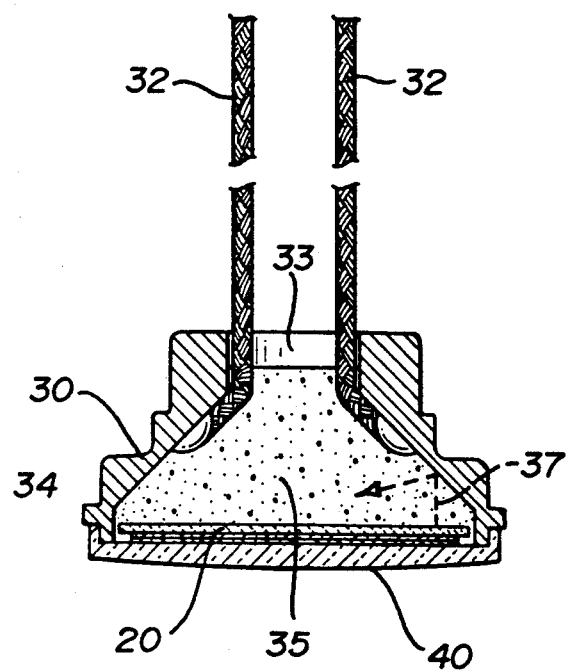
Figure 4A:
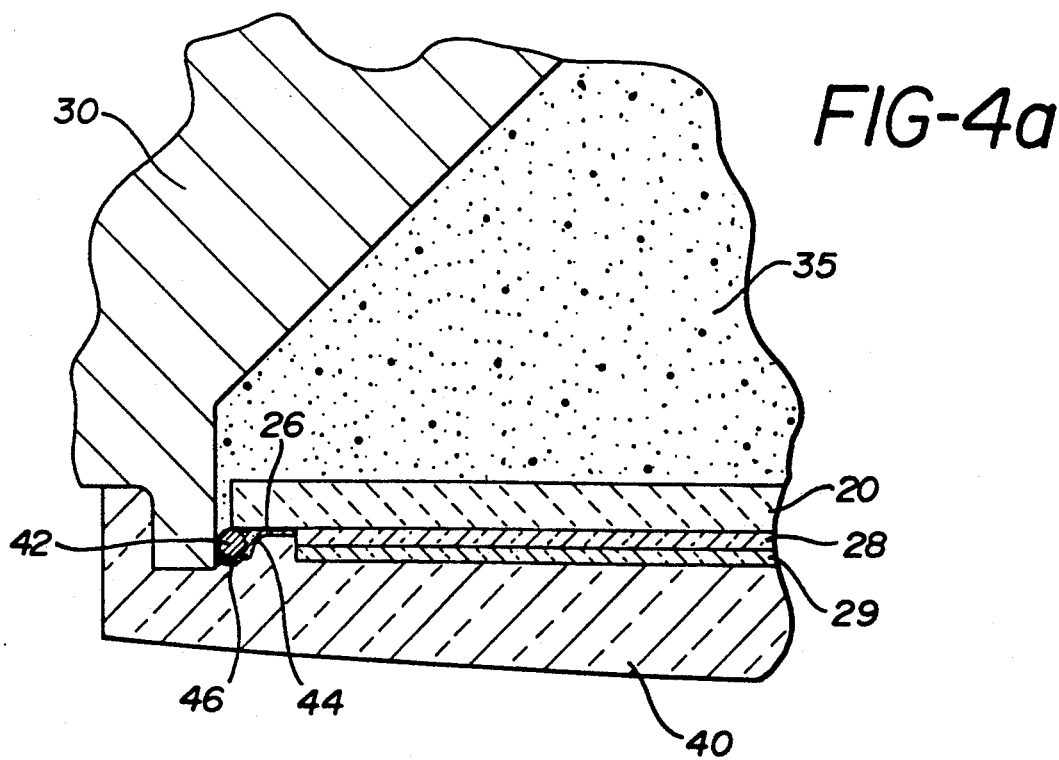
Figure 6:
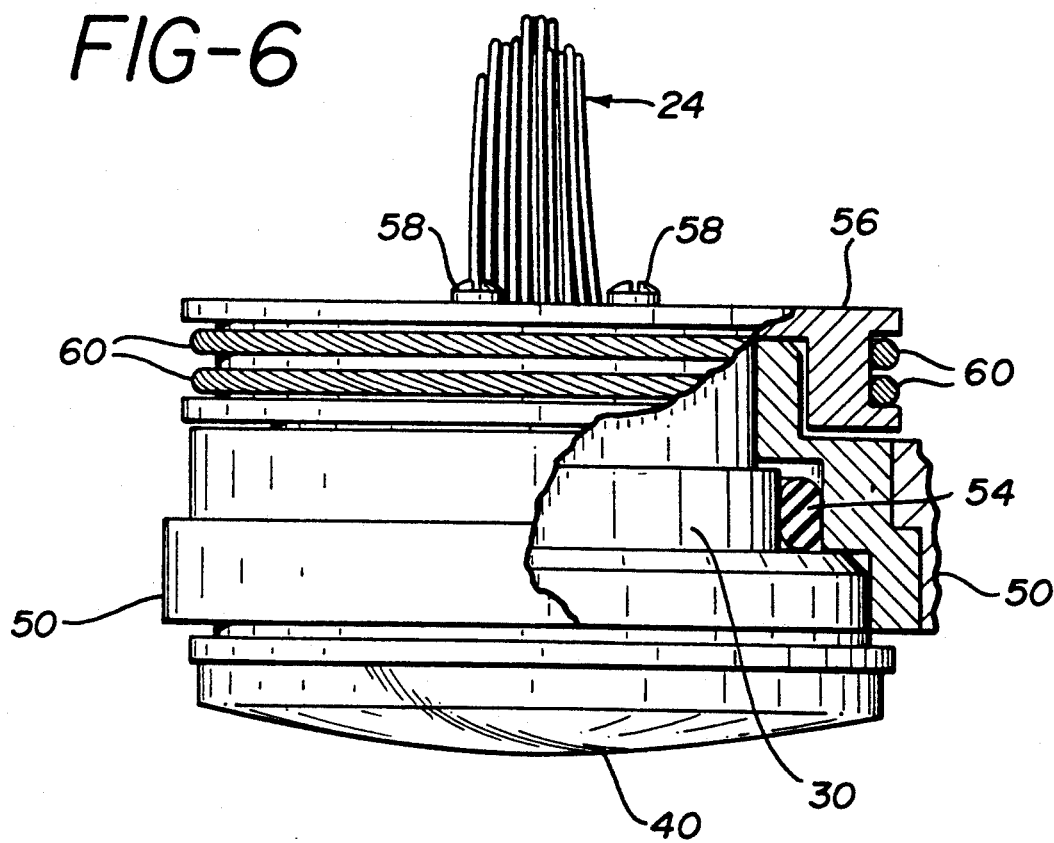
Figure 5:
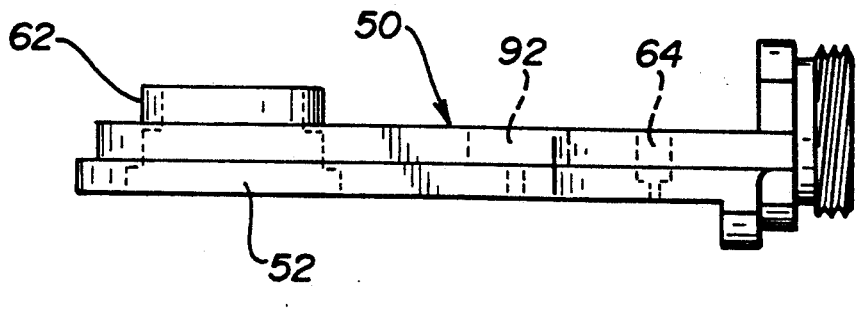
Figure 10:
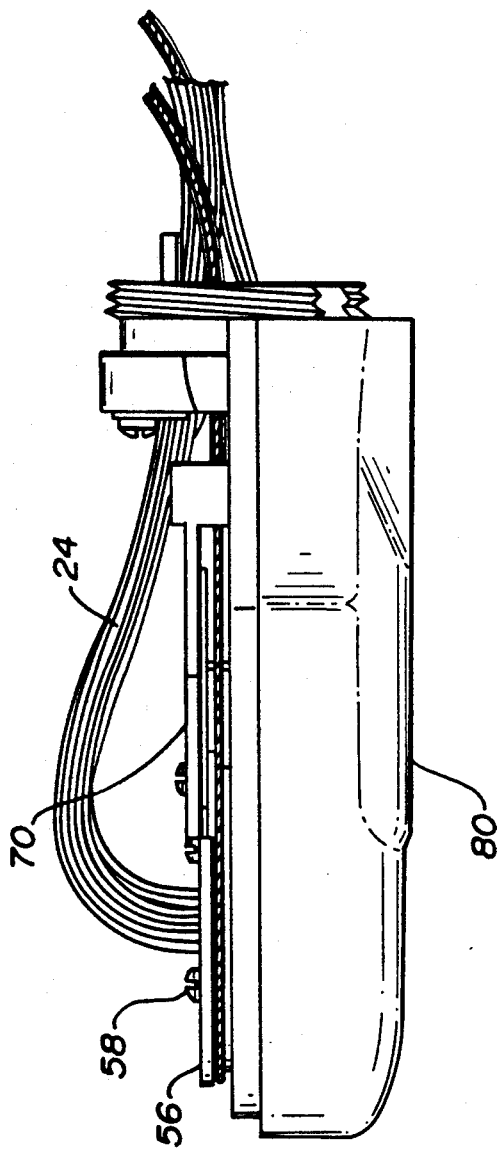
Figure 11:
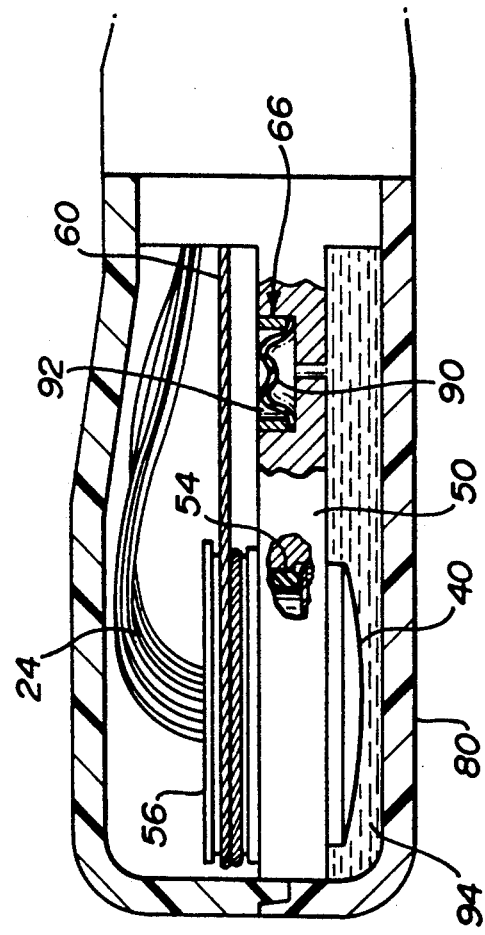

FIGS. 3a, 3b, and 3c illustrate details of construction of the round transducer array of the TEE scanhead of FIG. 1;

FIGS. 4 and 4a illustrate the round transducer array mounted in a bell-shaped housing filled with acoustic damping material;

FIG. 5 is a side view of the frame to which the bell-shaped housing and acoustic window of the TEE scanhead are attached;

FIG. 6 is a detailed side view of the bell-shaped housing mounted in the frame;

FIGS. 7 and 8 are top and side views of the assembled frame and bell-shaped housing showing the transducer wires and control cable;

FIG. 9 is a plan view of the acoustic window piece of the TEE scanhead;

FIGS. 10 and 11 show the acoustic window piece assembled onto the frame; and

Figure 12:
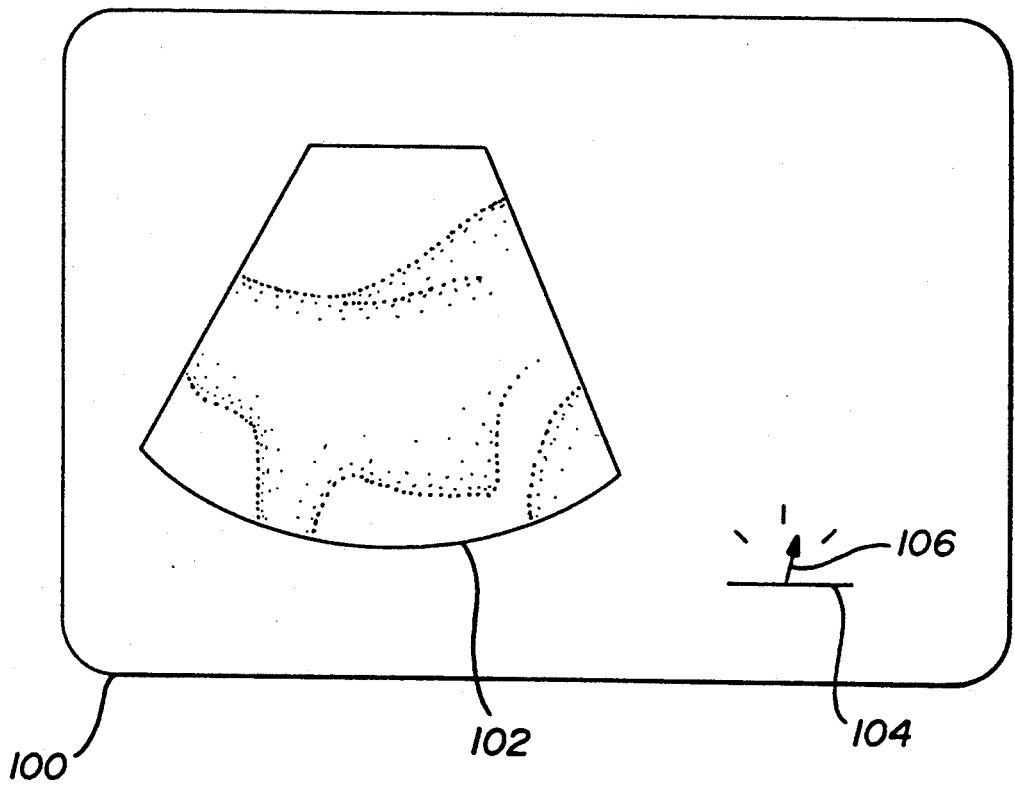

FIG. 12 depicts an image presentation displayed when using the TEE scanhead of the present invention.

Referring to FIG. 1, a transesophageal echocardiography (TEE) scanner of the present invention is shown. The scanner includes a distal end 1 which contains a rotating imaging transducer. The distal end is connected by a cable to a control unit 2 which has two control knobs 6 and 8. Control knob 6 is rotated to articulate the distal end 1 of the scanner. Control knob 8 is rotated to rotate the transducer in the distal end. The control unit 2 is connected by another cable to a connector 4 which connects to an ultrasound machine. The ultrasound machine actuates the transducer through wires in the scanner and receives ultrasonic echo information in return by way of the same wires. The echo information is used to develop a two dimensional image of structure or flow in the body which is in the imaging plane of the transducer.

Figure 2:
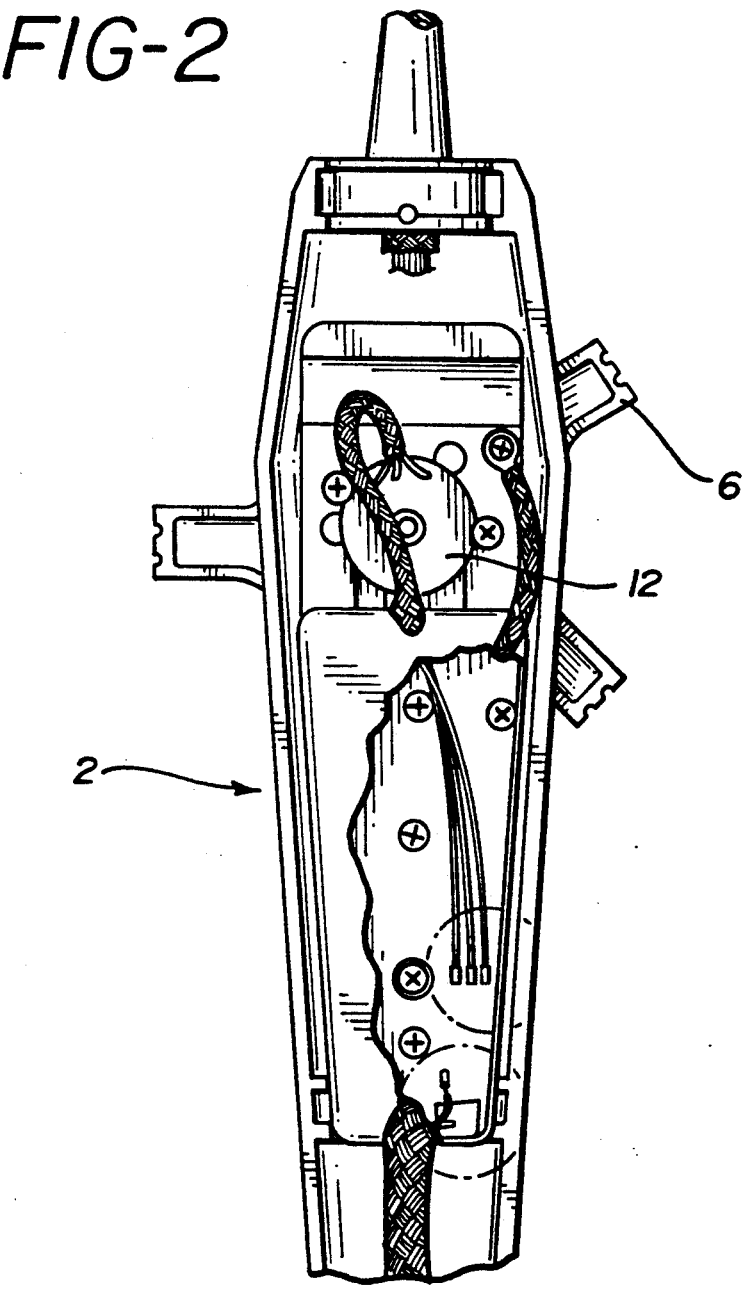
FIG. 2 is a bottom plan view of the control unit of FIG. 1a with the bottom cover removed.

FIG. 1a is a side view of the control unit 2 showing the lower cover 10. FIG. 2 is a view of the bottom of the control unit 2 with the lower cover removed. This FIGURE shows a potentiometer element 12, the wiper of which is mounted on the shaft of the control knob 8. Intermediate the knob 8 and the potentiometer element 12 inside the control unit 2 is a pulley which is mounted on the shaft of the knob 8. Connected to this pulley are two cables which run to the distal end of the scanner. As the knob 8 is turned this pulley rotates and pulls on one of the two cables in a reciprocal fashion. The force transmitted by these cables rotates the transducer at the distal end of the scanner. The knob is capable of rotation over approximately 180° to rotate the transducer over a similar angle. As the knob is turned it also turns the shaft and the potentiometer wiper. The variable resistance seen by the potentiometer wiper is transmitted to the ultrasound machine for display of the angular setting of the image plane as explained below.

The ultrasonic transducer at the distal end of the scanner is a phased array transducer having a round configuration. Referring to FIGS. 3a–3c, the transducer is formed by laminating two matching layers of epoxy 28 and 29 to a circular piezoelectric disc 20 having metallic electrodes 22 and 26 laminated to each side. The ceramic and electrodes are then cut into separate elongated elements 14 by sawing through the electrodes, ceramic and one of the matching layers 28. A cross-sectional view of three elements is shown in FIG. 3b. As FIG. 3a shows, the elements do not extend fully to the lateral ends of the disc; two inactive crescent-shaped areas 16 are left at the ends. The piezoelectric disc 20 is cut into the desired number of elements, such as 48 or 64 elements, and wires 24 are soldered to each of the back electrodes 24 for energizing and receiving echo information from the elements. The electrodes may have a uniform pitch (center to center spacing) or a variable pitch dependent upon considerations known in the art.

The transducer is mounted in a bell-shaped brass backing box 30 as shown in FIG. 4. Two grounding braids 32 which ground the backing box are soldered to the inner surface of the backing box as shown at 34. The grounding braids exit the interior of the backing box through an aperture 33 at the top of the box, as do the wires 24 (not shown) which are attached to the back electrodes 22 of the transducer elements. The interior of the backing box is filled with a high loss, elastomeric backing material 35 which is loaded with fillers for acoustic absorption and thermal conductivity. The curved and angular inner surface of the backing box reduces reverberation artifacts from the transducer by reflecting acoustic energy into the backing material rather than directly back to the transducer as indicated by the path of arrow 37. The front of the matching layer 29 is overlaid with an RTV silicone lens 40 having a spherical radius.

The front electrodes 26 of the phased array transducer are grounded in a novel manner which is shown in FIGS. 3c and 4a. The matching layers do not extend fully to the periphery of the transducer disc as FIG. 3c shows. Rather, the electrodes 26 are exposed at this outer periphery on the front side of the transducer. In FIG. 3c the tranducer is shown divided by a center line 31 into an upper half on side A and a lower half on side B. A grounding wire 42 extends completely around the outer periphery of the transducer disc 20 in contact with the element electrodes 26 and the backing box 30. Over one-half of the perimeter of the transducer the wire 42 is electrically and physically connected to the box and electrodes by silver epoxy 44. Over the other half of the perimeter the wire is soldered to the box and electrodes as indicated at 46 and overlaid with silver epoxy. The run of the grounding wire 42 starts and finishes at one of the large crescent-shaped ends 16, which affords ease in attaching the ends of the wire. This approach grounds one end of each element by one technique and the other end of each element by the other technique and provides an extra measure of electrical integrity and patient safety. The silver epoxy technique imposes no thermal stresses on the electrodes as soldering does, and soldering provides the best low resistance ground return. Alternatively, the wire 42 may be soldered completely around the perimeter of the transducer then overlaid with a layer of silver epoxy.

The backing box and transducer assembly is mounted in an aperture 52 (delineated in phantom) in a frame 50 as shown in FIGS. 5 and 6. An O-ring 54 is located between the frame 50 and the exterior of the box 30 to define the fluid chamber in which the transducer is located. A pulley 56 is fastened to the top of the backing box 30 by screws 58 and overlies a cylindrical projection 62 from the top of the frame 50. The other ends of the cables 60, referred to in the discussion of FIG. 2, are attached to the pulley and wrapped three-quarters of the way around the pulley. As the control knob 8 is turned the cables wind and unwind from the pulley 56 to rotate the pulley and the transducer/backing box assembly. This rotates the imaging plane of the transducer.

As FIG. 5 shows, the frame 50 has a second aperture 92 for a volume compensator 66 and a third aperture 64 for a fluid fill port.

FIGS. 7 and 8 are top plan and side views of the frame and transducer assembly. The transducer wires 24 and the control cables pass through an opening in the rear 51 of the frame. The control cables are enclosed in spring guides which terminate and are fastened by screws 72 and 74. Located above the control cables and shielding them is a wire guard 70. FIG. 7 also shows the screw cap of the fill port 64 and a portion of the volume compensator 66.

The transducer fluid chamber is enclosed by a urethane acoustic window piece 80, shown in FIGS. 8–11. FIGS. 5 and 8 show a lip that is beveled around the periphery of the top surface of the frame 50 and vertically at the rear 51 of the frame. The edge of the acoustic window piece 80 and this lip form a trough shown at 82 and 84 in FIG. 8. This trough is filled with a bead of adhesive to secure the acoustic window piece to the frame in a fluid-tight connection.

FIG. 9 shows that the interior of the acoustic window piece 80 includes a forward section 86 in which the transducer is located, and two projections 88 which project from the inner base of the piece and angle toward the rear with a separation between them. This defines a bubble trap compartment 89 in the rear of the piece. Bubbles floating through the separation between the projections will tend to float to the outer wall and be trapped in the rear compartment 89 by the projections 88 and away from the transducer section of the fluid chamber.

FIG. 11 shows the volume compensator 66 which includes a deformable silicone rubber diaphragm 90. Should the fluid inside the fluid chamber expand due to thermal, pressure, or other effects, the additional volume of the fluid will be accommodated by expansion of the silicone rubber diaphragm 90, which is adhesively affixed inside the aperture 92 of the frame 50 and ported to the fluid chamber.

FIG. 12 illustrates the display of the ultrasound machine which is presented during use of the scanner. The plane of the body which is being scanned is shown in the sector format of 102. In cardiology the conventional reference plane is a transverse plane, which is represented by cursor 104 on the display. As the transducer is rotated and its image plane rotates from the transverse orientation, the resistance of the potentiometer element 12 is sensed by the ultrasound machine and used to compute an angular indication cursor 106. This cursor 106 is displayed to provide the user with an indication of the angular orientation of the scanning plane 102 with respect to the transverse reference plane.

What is claimed is:

1. An ultrasonic scanner for scanning the body from within the body comprising:
    a circular shaped ultrasonic transducer comprising a plurality of elongated, parallel oriented, independently operable transducer elements, each of said elements having a substantially constant width along its length;
    a distal end on which said circular shaped ultrasonic transducer is rotatably mounted;
    a control unit including means for controlling the rotation of said ultrasonic transducer; and
    means, coupled between said distal end and said control unit, including means for operationally coupling said controlling means to said distal end.

2. The ultrasonic scanner of claim 1, wherein said circular shaped ultrasonic transducer further comprises crescent shaped elements at opposite sides of said transducer between which said parallel oriented transducer elements are located.

3. The ultrasonic scanner of claim 2, wherein said crescent shaped elements are inactive during actuation of said parallel oriented transducer elements.

4. The ultrasonic scanner of claim 1, wherein said circular shaped ultrasonic transducer further comprises a matching layer formed on one surface of said transducer, said matching layer having a circumference which is less than that of said circular shaped ultrasonic transducer so as to leave an exposed periphery about said transducer; and a grounding conductor extending about said exposed periphery and making electrical contact with said parallel oriented transducer elements.

5. The ultrasonic scanner of claim 1, further comprising a rotatable backing box having a first end on which said circular shaped ultrasonic transducer is mounted and a second end coupled to said operationally coupling means.

6. An ultrasonic scanner for scanning the body from within the body comprising:
an ultrasonic transducer;
a rotatable transducer mount filled with ultrasonic damping material for mounting said ultrasonic transducer with a back surface of said transducer opposing said damping material, said mount having an angled inner surface with respect to said transducer back surface, wherein reverberations travelling normal to said back surface toward said angled inner surface are generally reflected by said angled inner surface toward the center of said ultrasonic damping material;
a distal end on which said ultrasonic transducer and rotatable transducer mount are located;
a control unit including means for controlling the rotation of said rotatable transducer mount; and
means, coupled between said distal end and said control unit, including means for operationally coupling said controlling means to said distal end.

7. The ultrasonic scanner of claim 6, wherein said rotatable transducer mount has a conical inner surface.

8. The ultrasonic scanner of claim 6, wherein said rotatable transducer mount has a larger open end on which said ultrasonic transducer is mounted and a smaller, opposing open end through which electrical connections to said transducer pass.

9. The ultrasonic scanner of claim 8, wherein said operationally coupling means is coupled to said smaller end of said rotatable transducer mount.

10. An ultrasonic scanner for scanning the body from within the body comprising:
an ultrasonic transducer having an ultrasonic wave emitting surface;
a distal end on which said ultrasonic transducer is rotatably mounted with its emitting surface facing outwardly;
a control unit including means for controlling the rotation of said rotatable transducer mount; and
means, coupled between said distal end and said control unit, including means for operationally coupling said controlling means to said distal end; and
an ultrasonically transmissive cover overlaying said transducer so as to define an ultrasonic window opposing said transducer emitting surface; and
a bubble trap region adjacent said ultrasonic window and extending in the plane of the region between said ultrasonic window and said transducer emitting surface, into which bubbles between said ultrasonic window and said transducer emitting surface will travel and preferentially remain.

11. The ultrasonic scanner of claim 10, wherein said cover overlays both said transducer and said bubble trap region, said cover further including means for causing bubbles to preferentially remain in said bubble trap region.

12. The ultrasonic scanner of claim 11, wherein said means for causing comprises first and second extensions defining a bubble passageway therebetween and angled toward said bubble trap region.

* * * * *